(12) United States Patent
Rudman et al.

(10) Patent No.: US 10,603,020 B2
(45) Date of Patent: Mar. 31, 2020

(54) CENTERED BALLOON FOR THE LEFT ATRIAL APPENDAGE

(71) Applicant: BOSTON SCIENTIFIC SCIMED, INC., Maple Grove, MN (US)

(72) Inventors: Barry Rudman, Forest Lake, MN (US); Jan Weber, Maastricht (NL); Torsten Scheuermann, Munich (DE); Stephen Ruble, Lino Lakes, MN (US)

(73) Assignee: Boston Scientific Sciemed, Inc., Maple Grove, MN (US)

( * ) Notice: Subject to any disclaimer, the term of this patent is extended or adjusted under 35 U.S.C. 154(b) by 497 days.

(21) Appl. No.: 15/358,753

(22) Filed: Nov. 22, 2016

(65) Prior Publication Data

US 2017/0095238 A1 Apr. 6, 2017

Related U.S. Application Data

(63) Continuation of application No. 14/049,367, filed on Oct. 9, 2013, now abandoned.
(Continued)

(51) Int. Cl.
*A61B 17/00* (2006.01)
*A61F 2/24* (2006.01)
(Continued)

(52) U.S. Cl.
CPC ...... *A61B 17/0057* (2013.01); *A61B 17/1214* (2013.01); *A61B 17/12122* (2013.01);
(Continued)

(58) Field of Classification Search
CPC ............ A61M 29/02; A61B 17/12122; A61B 17/12022–12036; A61B 17/1214;
(Continued)

(56) References Cited

U.S. PATENT DOCUMENTS

| | | | | |
|---|---|---|---|---|
| 5,499,995 A | * | 3/1996 | Teirstein | .......... A61B 17/12022 606/192 |
| 6,994,092 B2 | * | 2/2006 | van der Burg | ..... A61B 17/0057 128/887 |

(Continued)

OTHER PUBLICATIONS

LabCE. https://www.labce.com/spg579126_red_blood_cell_rbc_size_variation.aspx. "Red Blood Cell (RBC) Size Variation". 2019.*

*Primary Examiner* — Wade Miles
*Assistant Examiner* — Mikail A Mannan
(74) *Attorney, Agent, or Firm* — Seager, Tufte and Wickhem LLP

(57) ABSTRACT

A medical device for reducing the volume of a left atrial appendage (LAA) may include an elongate shaft having a distal portion, and a volume-reducing means expandable from a collapsed to an expanded state, the volume-reducing means being releasably attached to the distal portion. The volume-reducing means may include an actuatable frame and an impermeable covering disposed over the frame. The volume-reducing means may be sized to fit within the LAA in the expanded state while maintaining an open fluid flow path from a distal region through the ostium of the LAA. A medical device may include a second volume-reducing means to be placed within and substantially occlude a distalmost region of the LAA. A method may include inserting a volume-reducing means into the LAA, expanding the volume-reducing means, and positioning the volume-reducing means such that an open fluid flow path is maintained through an entire cycle of the heart.

20 Claims, 21 Drawing Sheets

Related U.S. Application Data

(60) Provisional application No. 61/711,326, filed on Oct. 9, 2012.

(51) Int. Cl.
  *A61M 29/02* (2006.01)
  *A61F 2/01* (2006.01)
  *A61B 17/12* (2006.01)

(52) U.S. Cl.
  CPC ........ *A61B 17/12136* (2013.01); *A61F 2/013* (2013.01); *A61F 2/2487* (2013.01); *A61M 29/02* (2013.01); *A61B 17/12145* (2013.01); *A61B 17/12163* (2013.01); *A61B 2017/00632* (2013.01); *A61B 2017/12095* (2013.01); *A61B 2017/12127* (2013.01)

(58) Field of Classification Search
  CPC ........ A61B 17/12136; A61B 17/12145; A61B 17/12163; A61B 17/12095; A61B 17/12168; A61B 17/12172; A61B 17/12177; A61B 2017/1205; A61B 2017/12054; A61F 2/01; A61F 2/013; A61F 2002/016; A61F 2002/011; A61F 2002/015; A61F 2002/018
  See application file for complete search history.

(56) References Cited

U.S. PATENT DOCUMENTS

| | | |
|---|---|---|
| 7,597,704 B2 | 10/2009 | Frazier et al. |
| 7,713,282 B2 | 5/2010 | Frazier et al. |
| 7,727,189 B2 | 6/2010 | VanTassel et al. |
| 7,735,493 B2 | 6/2010 | van der Burg et al. |
| 7,862,500 B2 | 1/2011 | Khairkhahan et al. |
| 7,972,359 B2 | 7/2011 | Kreidler |
| 8,080,032 B2 | 12/2011 | van der Burg et al. |
| 2002/0022860 A1 | 2/2002 | Borillo et al. |
| 2003/0181942 A1 | 9/2003 | Sutton et al. |
| 2005/0038470 A1* | 2/2005 | van der Burg ..... A61B 17/0057 606/213 |
| 2005/0177182 A1 | 8/2005 | van der Burg et al. |
| 2007/0066993 A1 | 3/2007 | Kreidler |
| 2010/0049238 A1 | 2/2010 | Simpson |
| 2011/0098525 A1 | 4/2011 | Kermode et al. |
| 2012/0035643 A1 | 2/2012 | Khairkhahan et al. |
| 2012/0323267 A1* | 12/2012 | Ren ................. A61B 17/12172 606/191 |

\* cited by examiner

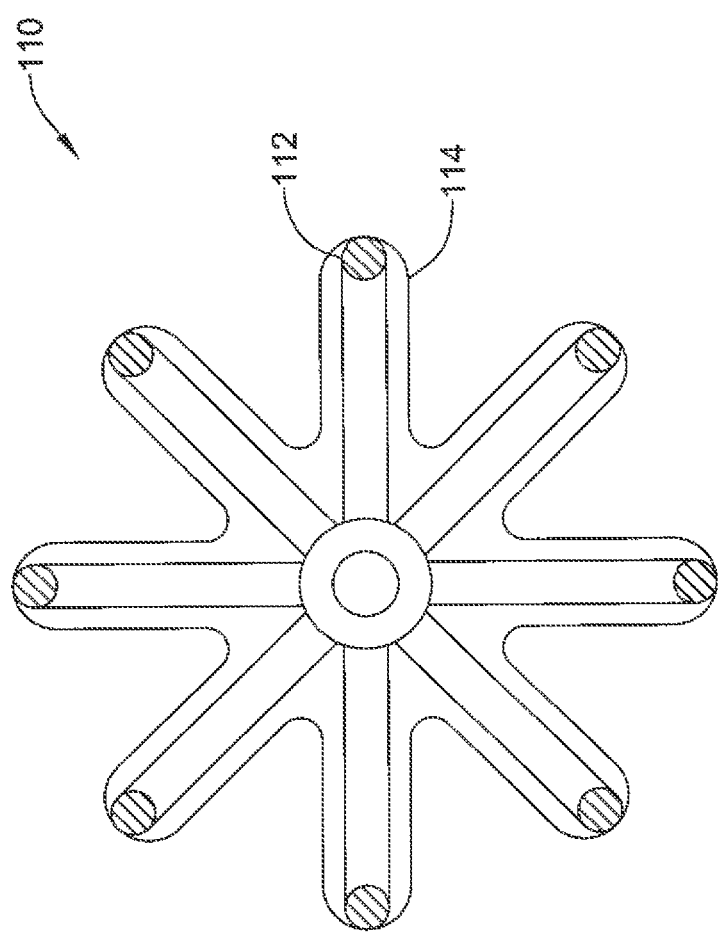

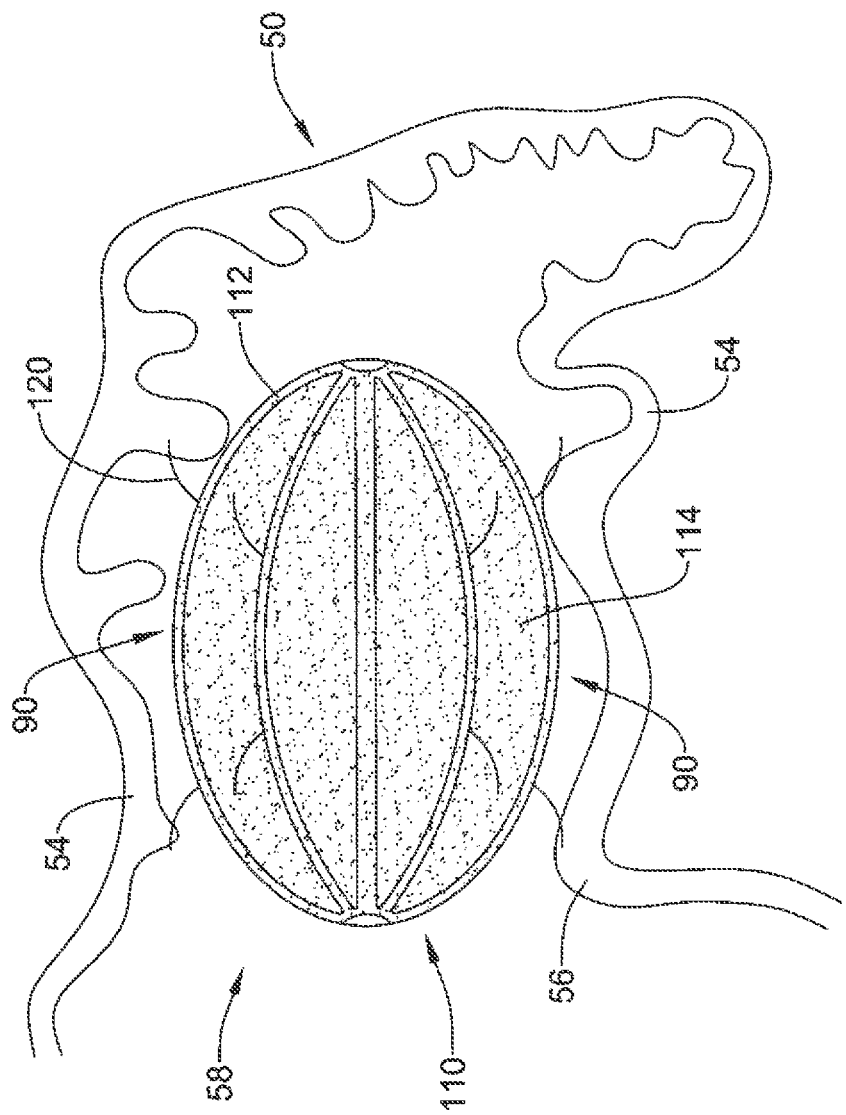

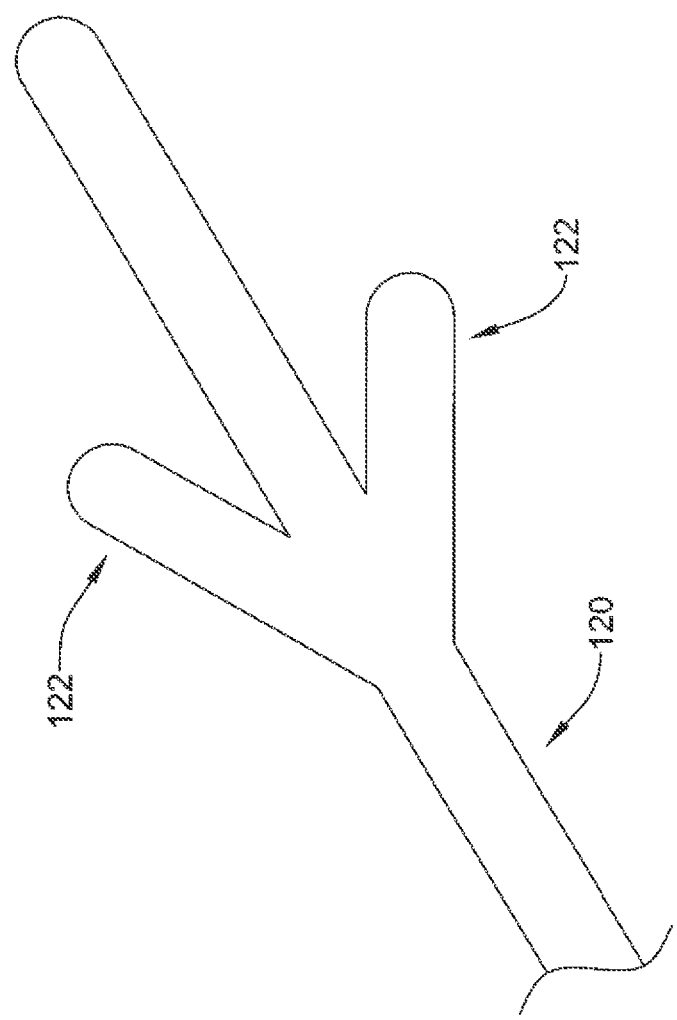

CENTERED BALLOON FOR THE LEFT ATRIAL APPENDAGE

CROSS-REFERENCE TO RELATED APPLICATIONS

This application is a continuation of U.S. application Ser. No. 14/049,367, filed Oct. 9, 2013, which claims priority to U.S. Provisional Application No. 61/711,326 filed Oct. 9, 2012.

TECHNICAL FIELD

The disclosure relates generally to percutaneous medical devices and more particularly to percutaneous medical devices for implantation into the left atrial appendage (LAA) of a heart.

BACKGROUND

The left atrial appendage is a small organ attached to the left atrium of the heart. During normal heart function, as the left atrium constricts and forces blood into the left ventricle, the left atrial appendage does the same. The ability of the left atrial appendage to contract assists with improved filling of the left ventricle, thereby playing a role in maintaining cardiac output. However, in patients suffering from atrial fibrillation, the left atrial appendage may not properly contract, causing stagnant blood to pool within its interior, which can lead to the undesirable formation of thrombi within the left atrial appendage. As the heart beats, blood from the left atrial appendage, instead of being actively expelled by contraction of the left atrial appendage, may be pulled out of the left atrial appendage via suction effect created by the expansion of the left ventricle, thereby pulling thrombi into the blood stream. Thrombi forming in the left atrial appendage may contribute to stroke. As a treatment, medical devices have been developed which close off the ostium of the left atrial appendage, effectively removing the left atrial appendage from the circulatory system and reducing or eliminating the amount of thrombi which may enter the blood stream from the left atrial appendage.

Unfortunately, the left atrial appendage provides certain positive effects and closing the left atrial appendage off has a series of negative side-effects. For example, stretch receptors of the left atrial appendage play a role in mediating thirst in hypovolemia. Effectively eliminating these receptors by closing off the left atrial appendage may cause hypertension. Additionally, the left atrial appendage modulates the relationship between pressure and volume. Left atrial appendage clamping leads to an increase in diastolic transmitral and pulmonary flow velocities, and to an increase in left atrial mean pressure and size. Further still, the left atrial appendage is an endocrine organ which releases atrial natriuretic peptide (ANP). Endothelial cells of the left atrial appendage are specialized in the production and release of natriuretic peptides. In healthy human hearts, atrial natriuretic peptide concentration may be 40-fold higher in the left atrial appendage than in the rest of the atrial free wall and in the ventricles. A continuing need exists for improved medical devices and methods to control thrombus formation within the left atrial appendage of patients suffering from atrial fibrillation while accommodating the positive functionality of the left atrial appendage.

SUMMARY

A medical device for reducing the volume of a left atrial appendage of a heart, the left atrial appendage having a generally longitudinal axis, a lateral wall, and an ostium forming a proximal mouth thereof, may include an elongate shaft having a distal portion, and a volume-reducing means expandable from a collapsed state to an expanded state, the volume-reducing means being releasably attached to the distal portion. The volume-reducing means may include an actuatable support frame and an impermeable covering disposed over the support frame. The volume-reducing means may be sized to fit within the left atrial appendage in the expanded state while maintaining an open fluid flow path from a distal region of the left atrial appendage through the ostium of the left atrial appendage.

A medical device for reducing the volume of a left atrial appendage of a heart, the left atrial appendage having a generally longitudinal axis, a lateral wall, and an ostium forming a proximal mouth thereof, may include an elongate shaft having a distal portion, a first volume-reducing means expandable from a collapsed state to an expanded state, the first volume-reducing means being releasably attached to the distal portion, and a second volume-reducing means expandable from a collapsed state to an expanded state, the second volume reducing means being releasably attached to the distal portion. The first volume-reducing means and the second volume-reducing means may each include an actuatable support frame and an impermeable covering disposed over the support frame. The first volume-reducing means may be sized to fit within the left atrial appendage in the expanded state while maintaining an open fluid flow path from a distal region of the left atrial appendage through the ostium of the left atrial appendage. The second volume-reducing means may be configured to be placed within and substantially occlude a distalmost region of the left atrial appendage.

A method of reducing the volume of a left atrial appendage of a heart, the left atrial appendage having a generally longitudinal axis, a lateral wall, and an ostium forming a proximal mouth thereof, may include the steps of: obtaining a medical device having an elongate shaft having a distal portion, and a volume-reducing means expandable from a collapsed state to an expanded state, the volume-reducing means being releasably attached to the distal portion, wherein the volume-reducing means includes an actuatable support frame and an impermeable covering disposed over the support frame, wherein the volume-reducing means is sized to fit within the left atrial appendage in the expanded state; advancing the medical device percutaneously toward the heart; inserting the volume-reducing means through the ostium and into the left atrial appendage in the collapsed state; actuating the support frame to expand the volume-reducing means to the expanded state; introducing an inflation medium into an interior of the volume-reducing means; positioning the volume-reducing means such that an open fluid flow path from a distal region of the left atrial appendage through the ostium of the left atrial appendage is maintained through an entire cycle of the heart; detaching the volume-reducing means from the distal portion of the elongate shaft; and withdrawing the elongate shaft from the heart.

BRIEF DESCRIPTION OF THE DRAWINGS

FIG. 4C is a schematic partial cross-sectional view of the example medical device of FIG. 3;

FIG. 5 illustrates the example medical device of FIG. 3 disposed within the example left atrial appendage of FIG. 2;

FIGS. 11A-11D are schematic perspective views of example anchoring means for the example medical device of FIG. 3.

Figure 1:
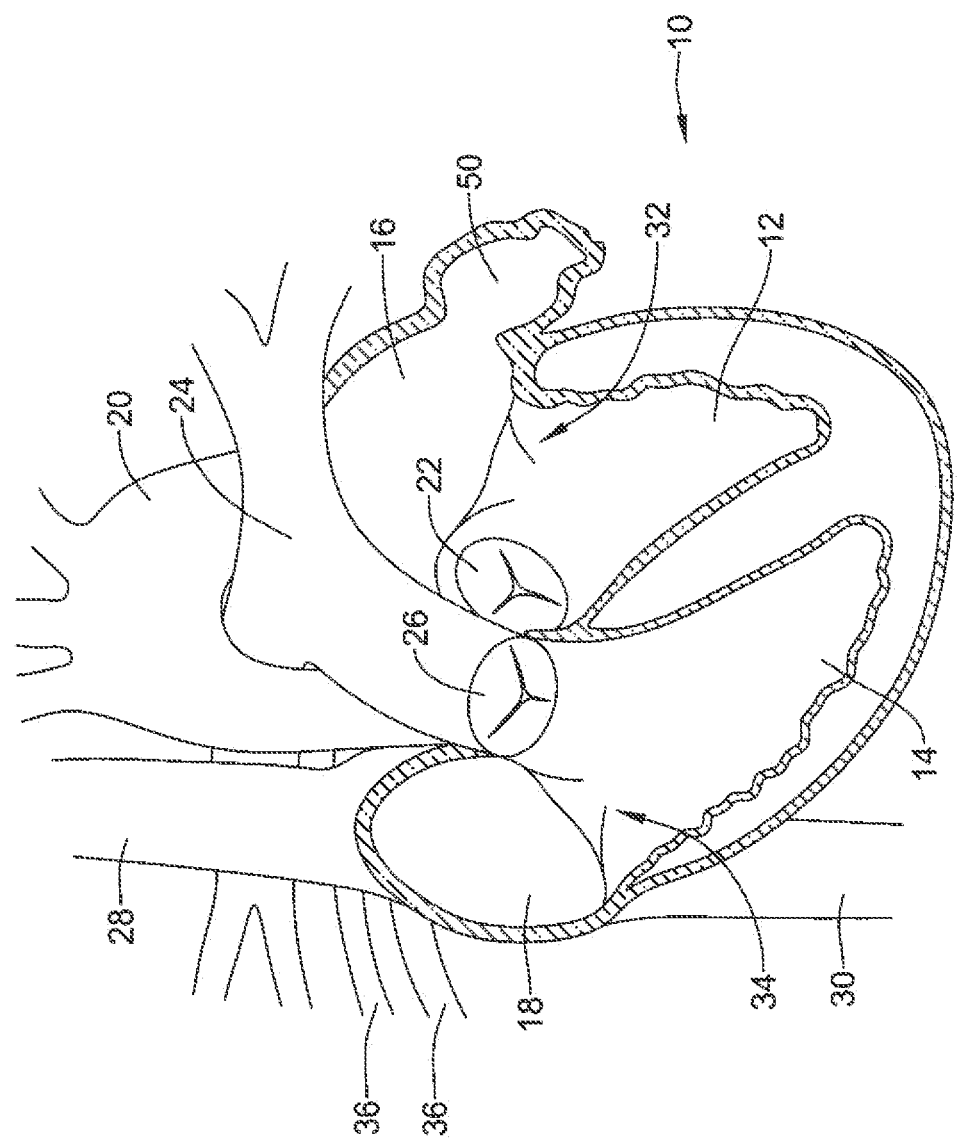
FIG. 1 is a schematic partial cross-sectional view of a heart.

While the invention is amenable to various modifications and alternative forms, specifics thereof have been shown by way of example in the drawings and will be described in greater detail below. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range, including the endpoints (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

The occurrence of thrombi in the left atrial appendage (LAA) during atrial fibrillation may be due to stagnancy of the blood pool in the LAA. The blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. Further, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and maintain blood flow out of the left atrial appendage, a medical device has been developed that reduces the interior volume of the left atrial appendage without closing the left atrial appendage completely off from the heart and/or circulatory system. In reducing the volume of the interior of the left atrial appendage, less blood is present within the left atrial appendage. As such, the suction effect of the left ventricle, either alone or in combination with contraction of the left atrium and/or left atrial appendage, may be sufficient to empty the left atrial appendage and prevent stagnant pooling of blood within the interior of the left atrial appendage. By reducing or elimination the stagnant pooling of blood, the formation of thrombi can be significantly reduced or avoided, thereby lowering the risk of stroke due to thrombolytic material entering the blood stream from the left atrial appendage.

Turning to the drawings, FIG. 1 is a partial cross-sectional view of certain elements of a human heart 10 and some immediately adjacent blood vessels. A heart 10 may include a left ventricle 12, a right ventricle 14, a left atrium 16, and a right atrium 18. An aortic valve 22 is disposed between the left ventricle 12 and an aorta 20. A pulmonary or semi-lunar valve 26 is disposed between the right ventricle 14 and a pulmonary artery 24. A superior vena cava 28 and an inferior vena cava 30 return blood from the body to the right atrium 18. A mitral valve 32 is disposed between the left atrium 16 and the left ventricle 12. A tricuspid valve 34 is disposed between the right atrium 18 and the right ventricle 14. Pulmonary veins 36 return blood from the lungs to the left atrium 16. A left atrial appendage (LAA) 50 is attached to and in fluid communication with the left atrium 16.

Figure 2:
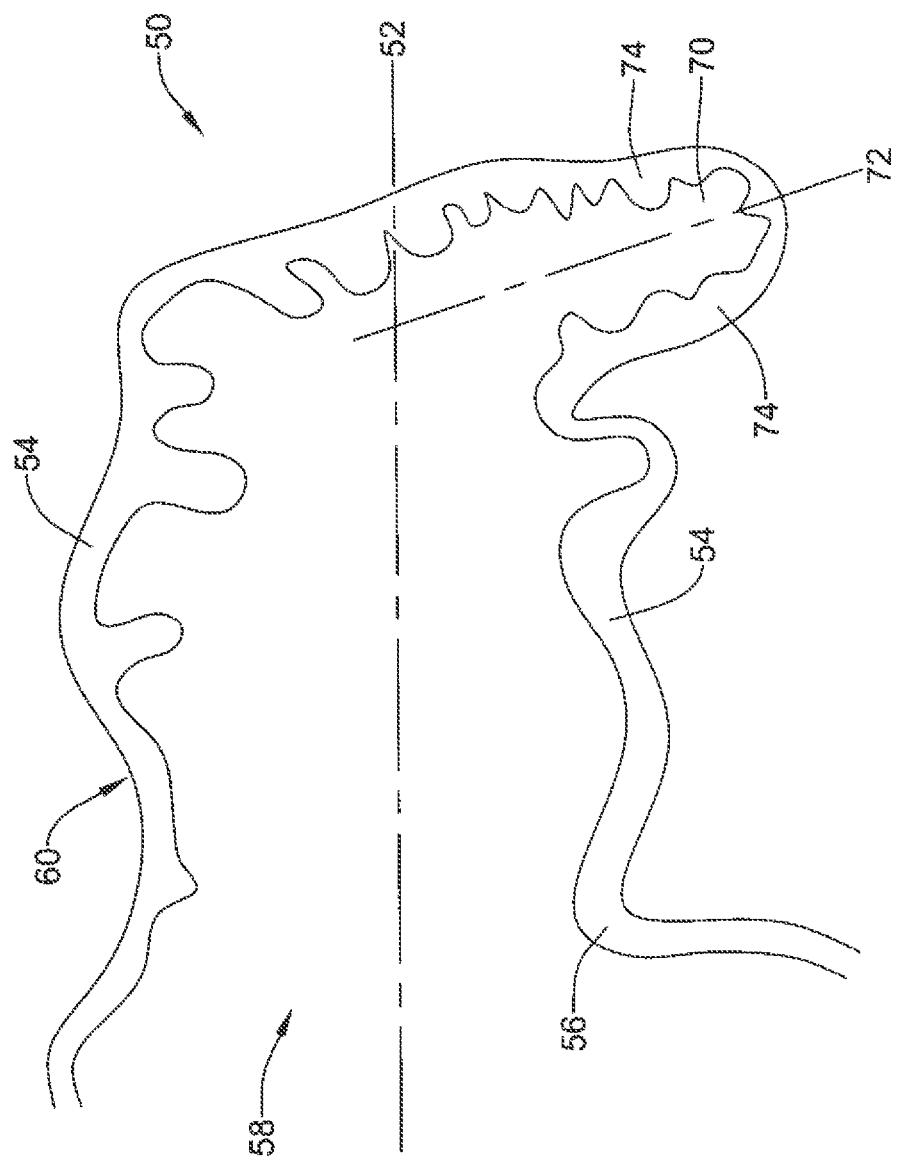
FIG. 2 is a schematic partial cross-sectional view of an example left atrial appendage.

FIG. 2 is a partial cross-sectional view of an example left atrial appendage 50. As discussed above, the left atrial appendage 50 may have a complex geometry and/or irregular surface area. Those skilled in the art will recognize that the illustrated LAA is merely one of many possible shapes and sizes for the LAA, which may vary from patient to patient. Those of skill in the art will also recognize that the medical devices and methods disclosed herein may be adapted for various sizes and shapes of the LAA, as necessary. A left atrial appendage 50 may include a generally longitudinal axis 52 arranged along a depth of a main body 60 of the left atrial appendage 50. The main body 60 may include a lateral wall 54 and an ostium 56 forming a proximal mouth 58. In some embodiments, a lateral extent of the ostium 56 and/or the lateral wall 54 may be smaller or less than a depth of the main body 60 along the longitudinal axis 52, or a depth of the main body 60 may be greater than a lateral extent of the ostium 56 and/or the lateral wall 54. In some embodiments, the left atrial appendage 50 may include a distalmost region 70, which may be formed or arranged as a tail-like element associated with a distal portion of the main body 60. In some embodiments, the distalmost region 70 may protrude radially or laterally away from the longitudinal axis 52 along a longitudinal axis 72. The distalmost region 70 may include a lateral wall 74. In some embodiments, a lateral extent of the lateral wall 74 of the distalmost region 70, as measured from the longitudinal axis 72 arranged along a depth of the distalmost region 70 from the main body 60 of the left atrial appendage 50, may be less than the lateral extent of the ostium 56 and/or the lateral wall 54.

Figure 3:
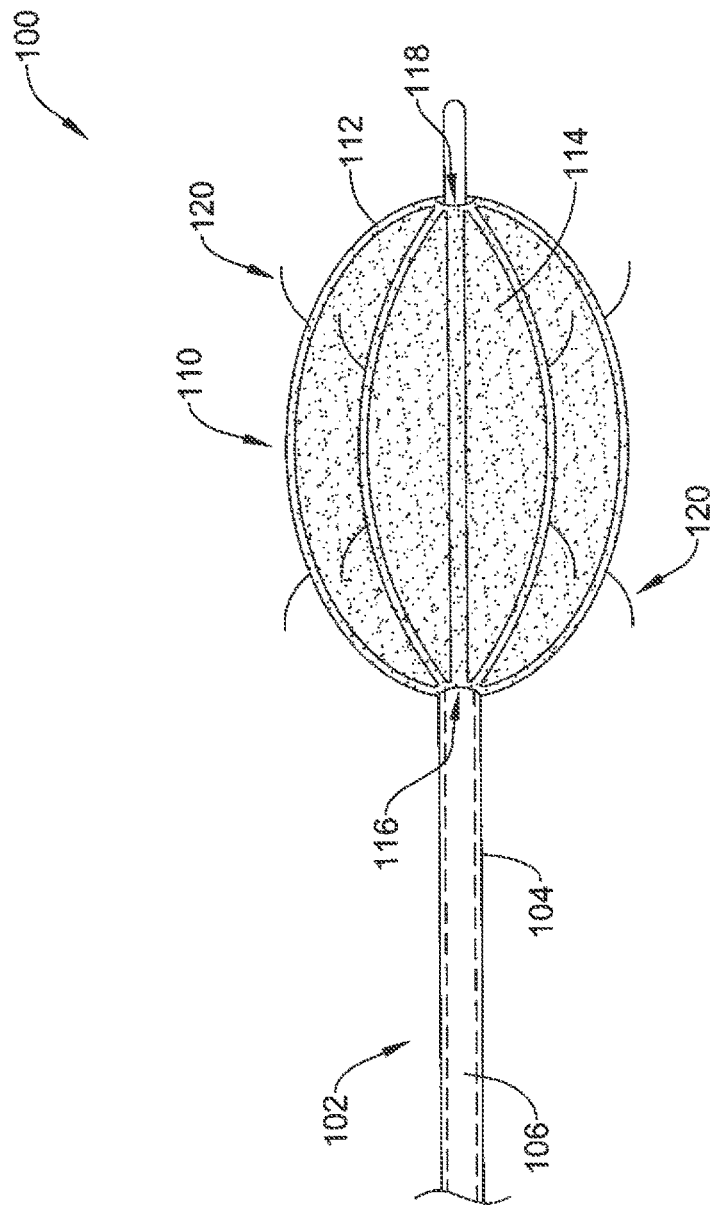
FIG. 3 is a schematic perspective view of an example medical device.

FIG. 3 generally illustrates a medical device 100 including an elongate shaft 102 having a distal portion 104 and a lumen 106 disposed therethrough, which may function as an inflation lumen in some embodiments. A volume-reducing means 110 may be disposed about and/or releasably attached to the distal portion 104. In some embodiments, the distal portion 104 may include a first section having a first diameter, and a second section distal of the first section having a second diameter less than the first diameter. In some embodiments, the elongate shaft 102 may include an outer shaft having an outer shaft diameter and an inner shaft disposed within a lumen of the outer shaft, the inner shaft having an inner shaft diameter that is less than the outer shaft diameter. In some embodiments, the inner shaft may be a guidewire slidably disposed within the lumen of the outer shaft.

The volume-reducing means 110 may be expandable from a collapsed state to an expanded state. The volume-reducing means 110 may include an actuatable support frame 112 and an impermeable covering 114 disposed over the actuatable support frame 112. In some embodiments, the actuatable support frame 112 may include a plurality of struts extending from a proximal hub 116 to a distal hub 118. In some embodiments, the actuatable support frame 112 may include a plurality of self-expanding struts. In some embodiments, the actuatable support frame 112 may include a mechanical means of actuating the plurality of struts. In the expanded state, the plurality of struts may bow radially outward relative to a longitudinal axis of the elongate shaft 102. While not explicitly illustrated, in some embodiments, the impermeable covering 114 may be disposed between individual struts of the actuatable support frame 112 or the impermeable covering 114 may be disposed within the actuatable support frame 112.

A volume-reducing means 110 may include an anchoring means configured to engage the lateral wall 54 of the left atrial appendage 50. In some embodiments, the anchoring means may include a plurality of anchoring members 120 extending outwardly from an outer surface of the volume-reducing means 110. In some embodiments, the plurality of anchoring members 120 may each include a means of limiting penetration of the plurality of anchoring members 120 into the lateral wall 54 of the left atrial appendage 50. In some embodiments, the plurality of anchoring members 120 may be configured to rest against a surface of the lateral wall 54. In some embodiments, the plurality of anchoring members 120 may be configured to penetrate the lateral wall 54. In some embodiments, the plurality of anchoring members 120 may each include a first portion that is configured to penetrate the lateral wall 54 and a second portion that is configured to rest against a surface of the lateral wall 54.

While not expressly illustrated, in some embodiments, the anchoring means may include one or more substantially stiff anchoring members protruding distally from the distal hub 118 or another portion of the volume-reducing means 110, wherein the one or more anchoring members are configured to penetrate a wall of the left atrial appendage 50. Additionally, the volume-reducing means 110 may include a plurality of centering elements protruding outwardly from an outer surface of the volume-reducing means 110. The plurality of centering elements may be configured to engage the lateral wall 54 of the left atrial appendage 50. (OTHER ANCHORING MECHANISMS?)

In some embodiments, the lumen 106 of the elongate shaft 102 may be in fluid communication with an interior of the volume-reducing means 110. In some embodiments, the volume-reducing means 110 may include a means of introducing an inflation medium into the interior of the volume-reducing means 110 while preventing the inflation medium from exiting the interior of the volume-reducing means 110. In some embodiments, the means of introducing an inflation medium into the interior of the volume-reducing means 110 may be disposed at the proximal hub 116. In some embodiments, the means of introducing may include a hemostatic valve, a one-way valve, a covering flap, or other suitable means of permitting the inflation medium to enter the interior of the volume-reducing means 110 without permitting the inflation medium to exit the interior of the volume-reducing means 110.

In some embodiments, the inflation medium may include a liquid, a viscous gel, an adhesive or glue, or other fluid suitable for inflating the volume-reducing means 110. In some embodiments, the inflation medium may be configured to at least partially solidify within the interior of the volume-reducing means 110. In some embodiments, the inflation medium may be configured to completely solidify within the interior of the volume-reducing means 110. In embodiments where the inflation medium is configured to partially or completely solidify, the inflation medium may be configured to solidify over time (i.e., a time-delayed hardening), or a catalyst may be injected into the volume-reducing means 110 which causes the inflation medium to solidify through physical, chemical, or other reaction(s).

Figure 4A:
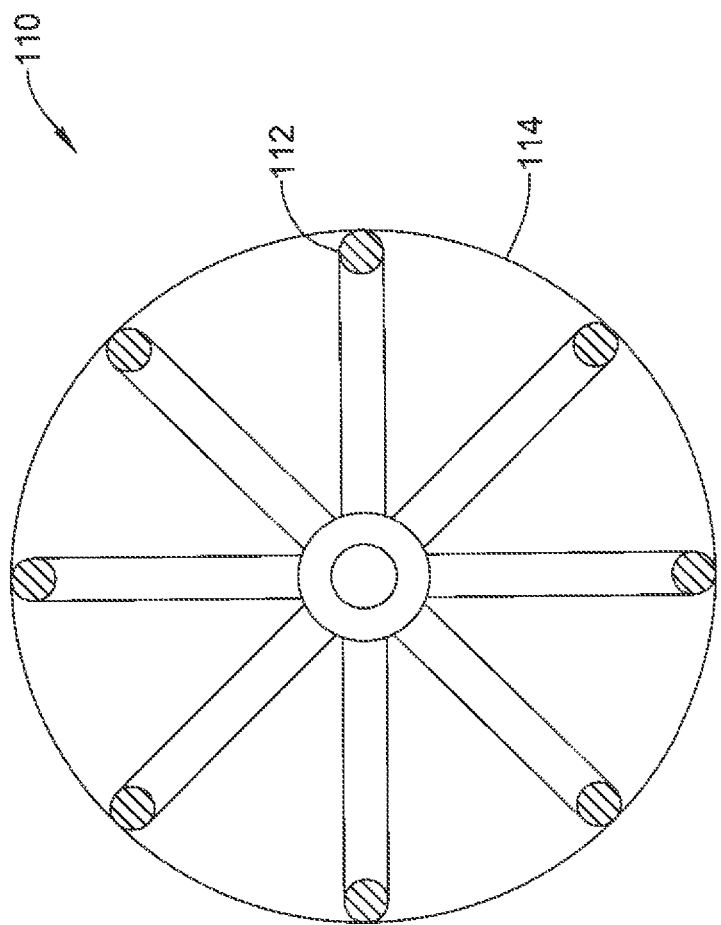
FIG. 4A is a schematic partial cross-sectional view of the example medical device of FIG. 3.
Figure 4B:
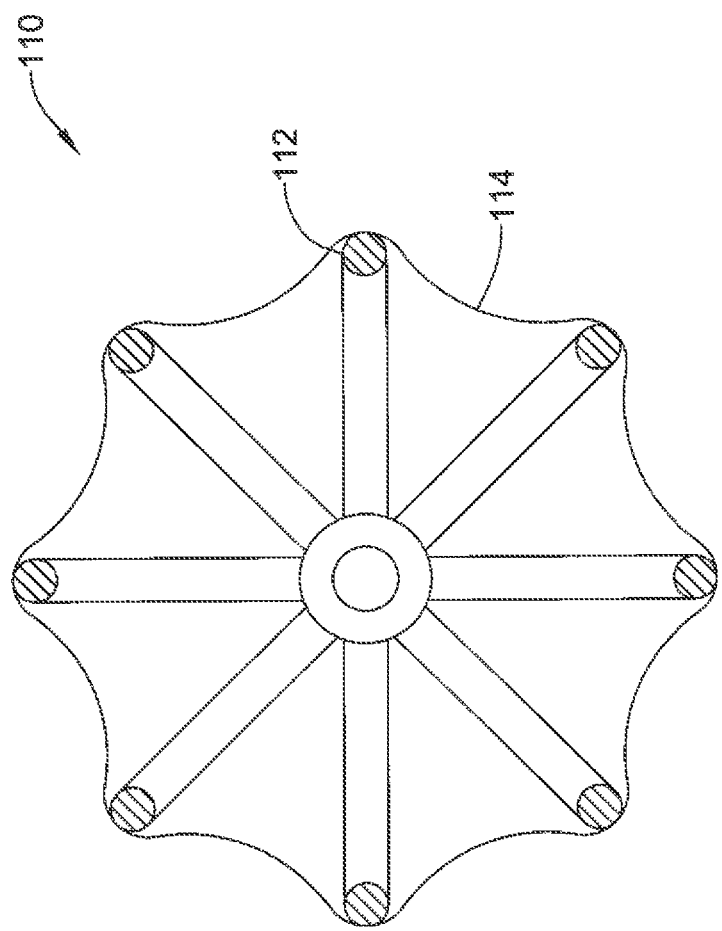
FIG. 4B is a schematic partial cross-sectional view of the example medical device of FIG. 3.

FIGS. 4A-4C illustrate cross-sectional views of example volume-reducing means 110. The volume-reducing means 110 of FIG. 4A includes an impermeable covering 114 that is stretched taut or tightly about the actuatable support frame 112. The volume-reducing means 110 of FIG. 4B includes an impermeable covering 114 that is scalloped between individual struts of the actuatable support frame 112 or partially loose about the actuatable support frame 112. The volume-reducing means 110 of FIG. 4C includes an impermeable covering 114 that is disposed closely about or adhered to the individual struts of the actuatable support frame 112.

FIGS. 4A-4C may also be considered to illustrate various states of inflation of a volume-reducing means 110. For example, FIG. 4C may show an early stage of deployment, prior to the introduction of the inflation medium into the interior of the volume-reducing means 110, where the actuatable support frame 112 has been expanded to the expanded state but the impermeable covering 114 remains in the collapsed state. FIG. 4B may be considered to show partial inflation of the volume-reducing means 110, where the actuatable support frame 112 is shown in the expanded state and the impermeable covering 114 is in the process of moving from the collapsed state to the expanded state as the inflation medium is introduced into the interior of the volume-reducing means 110. FIG. 4C may be considered to illustrate a fully inflated volume-reducing means 110 in the expanded state.

As illustrated in FIG. 5, the volume-reducing means 110 may be sized to fit within the left atrial appendage 50 in the expanded state while maintaining an open fluid flow path 90 from a distal region of the left atrial appendage 50 through the ostium 56 of the left atrial appendage 50. In some embodiments, the plurality of anchoring members 120 may maintain the volume-reducing means 110 in a spaced-apart relationship with the lateral wall 54 of the left atrial appendage 50. In some embodiments, the open fluid flow path 90 may be disposed between an outer surface of the volume-reducing means 110 and the lateral wall 54 of the left atrial appendage 50. In some embodiments, the volume-reducing means 110 may be configured to maintain the open fluid flow path 90 during an entire cycle of the heart 10.

As also seen in FIG. 5, the volume-reducing means 110, when implanted and inflated to the expanded state, may reduce the volume of an interior of the left atrial appendage 50. In some embodiments, the volume-reducing means 110 may be sized to reduce the volume of the left atrial appendage by at least 40%, by at least 50%, by at least 65%, by at least 75%, by at least 90%, or other suitable amounts as desired. Reducing the volume of the left atrial appendage 50 may aid in reducing thrombi formation within the left atrial appendage 50 while maintaining the open fluid flow path 90 permits the left atrial appendage 50 to continue to provide natriuretic peptides to the blood steam.

Figure 6:
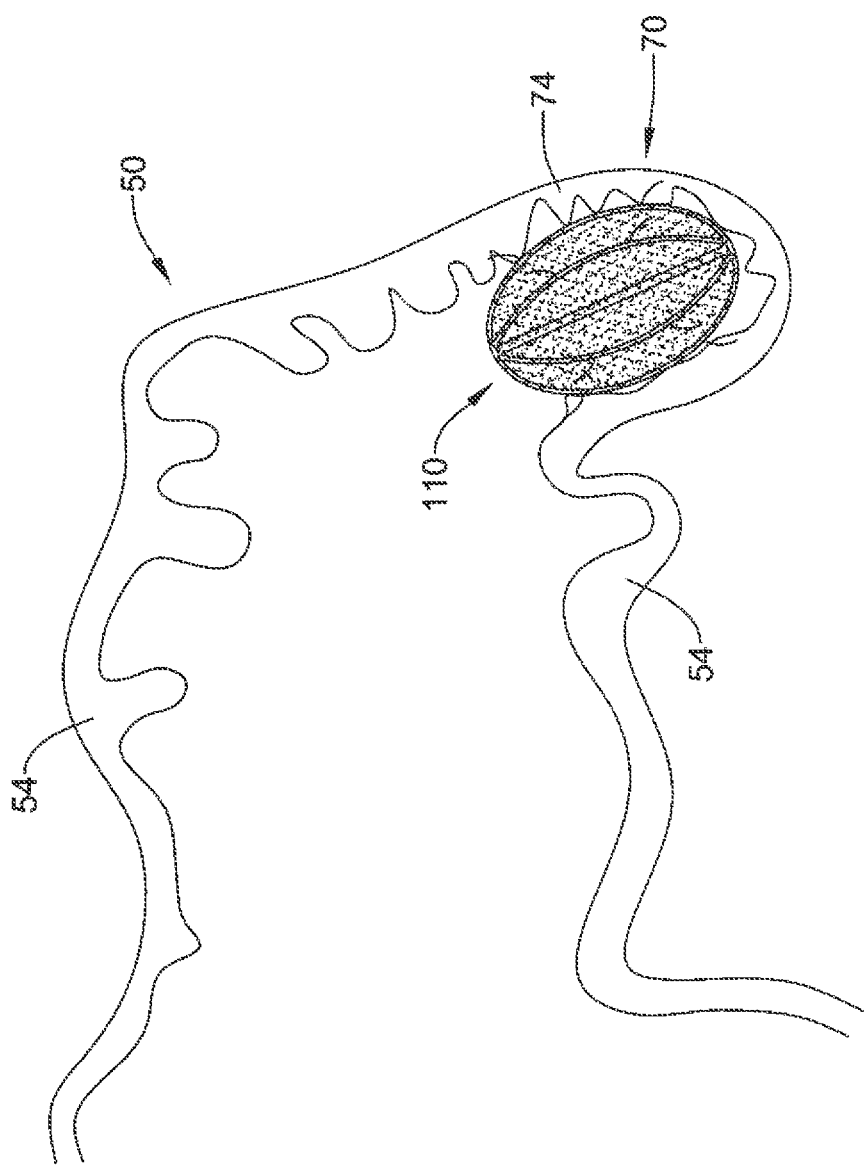
FIG. 6 illustrates the example medical device of FIG. 3 disposed within the example left atrial appendage of FIG. 2.

In some embodiments, the volume-reducing means 110 may be sized and configured to be disposed within a distalmost region 70 of the left atrial appendage 50, and in some embodiments to substantially engage the lateral wall 74 of the distalmost region 70, as seen in FIG. 6. In some embodiments, the volume-reducing means 110 may substantially occlude the distalmost region 70 of the left atrial appendage 50. As the distalmost region 70 may sometimes be oriented away from the main body 60, proper blood flow out of the distalmost region 70 may be difficult to maintain during atrial fibrillation and/or improper or incomplete contraction of the left atrial appendage 50. As such, occluding the small tail-like distalmost region 70 may reduce the occurrence of thrombi formation due to stagnant blood within the distalmost region 70, while still permitting the left atrial appendage 50 to produce and release natriuretic peptides into the blood stream.

Figure 7A:
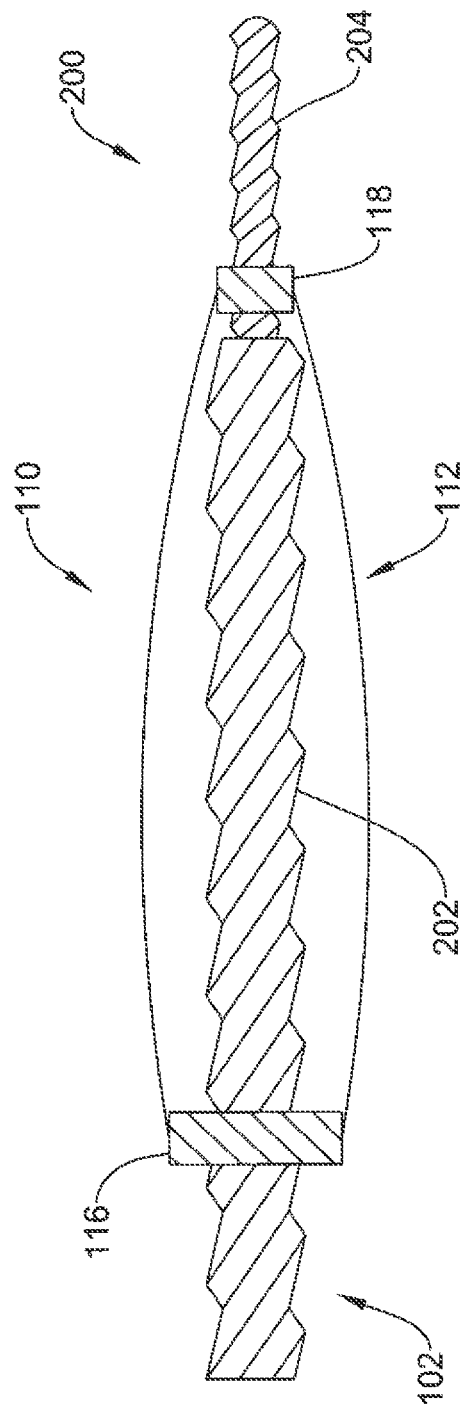
FIGS. 7A-7C are schematic partial cross-sectional views of an example mechanism for actuating the example medical device of FIG. 3.
Figure 7B:
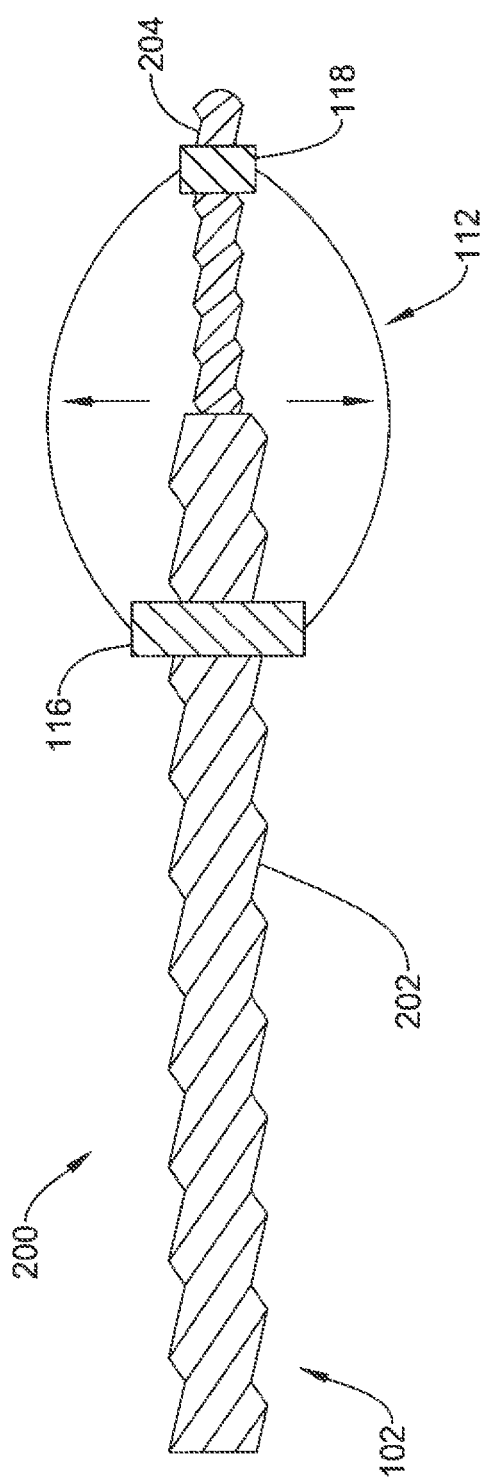
Figure 7C:
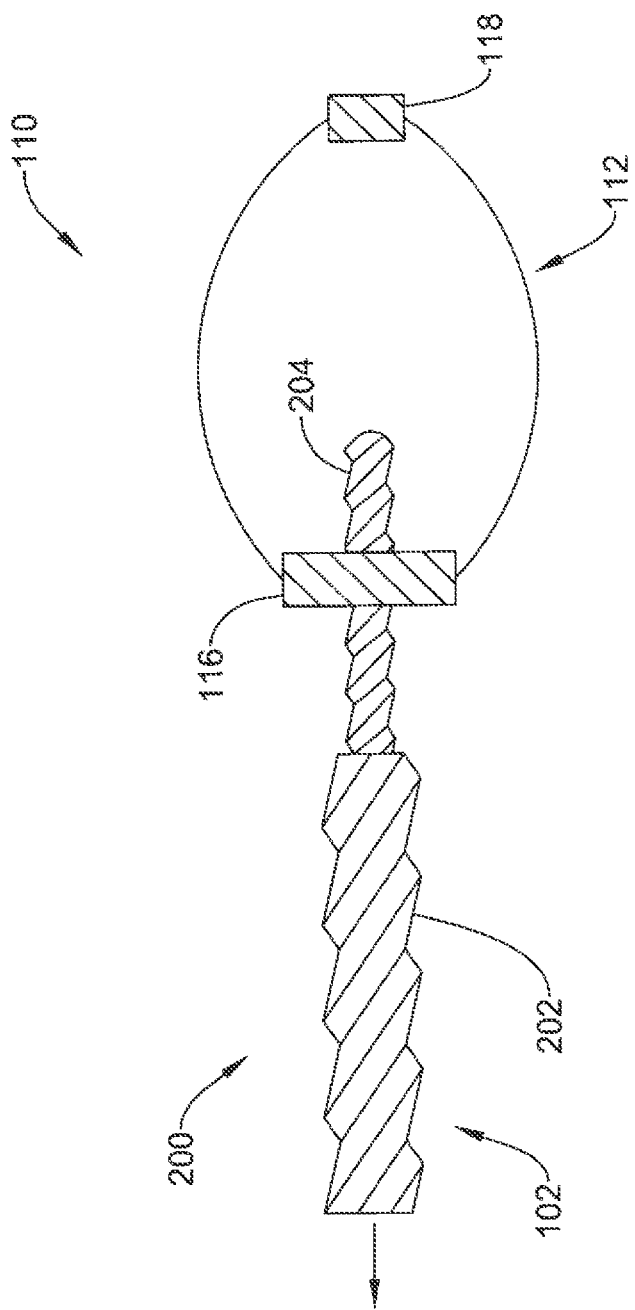

FIGS. 7A-7C illustrate an example mechanical means 200 of actuating the actuatable support frame 112 of the volume-reducing means 110. A distal portion 104 of an elongate shaft 102 may include a first threaded region 202 and a second threaded region 204. The first threaded region 202 may have a first thread pitch and a first outer extent. The second threaded region 204 may have a second thread pitch less than the first thread pitch and a second outer extent less than the first outer extent, such that equal rotation of the first threaded region 202 and the second threaded region 204 results in a first mating element, such as proximal hub 116, traveling farther on the first threaded region 202 than a second mating element, such as distal hub 118, travels on the second threaded region 204, thereby forcing the plurality of struts to bow radially outward.

FIG. 7A illustrates the volume-reducing means 110 in the collapsed state, such as during delivery of the medical device 100 to the left atrial appendage 50. FIG. 7B illustrates the proximal hub 116 advancing distally along the first threaded region 202 farther than the distal hub 118 advances distally along the second threaded region 204, thereby actuating the actuatable support frame 112 toward the expanded state. FIG. 7C illustrates a partial release of the volume-reducing means 110 from the elongate shaft 102. After the proximal hub 116 and the distal hub 118 reach a distal end of their respective threaded regions, the elongate shaft 102 is withdrawn proximally, thereby separating the volume-reducing means 110 from the elongate shaft 102. The second threaded region 204 passes through the proximal hub 116, which is sized to engage the first threaded region 202. As noted above, the first threaded region 202 has a first outer extent that is greater than a second outer extent of the second threaded region 204. Therefore, the second threaded region 204 may pass through the proximal hub 116 without engaging the proximal hub 116. After the elongate shaft 102 has been withdrawn from the volume-reducing means 110, the means of introducing an inflation medium into the interior of the volume-reducing means 110 may close thereby preventing blood from entering the interior or inflation medium from exiting the interior of the volume-reducing means 110. In some embodiments, a means of introducing an inflation medium into the interior of the volume-reducing means 110 while preventing the inflation medium from exiting the interior of the volume-reducing means 110 may be disposed at the proximal hub 116 and at the distal hub 118.

Regardless of whether the volume-reducing means 110 is expanded to the expanded state by a self-expanding support frame, by a mechanically-actuated support frame, by inflation or filling of an interior of the volume-reducing means 110, or by another suitable means, the volume-reducing means 110 in the expanded state remains impermeable to blood, thereby reducing the overall blood-carrying volume of the left atrial appendage 50.

Figure 8:
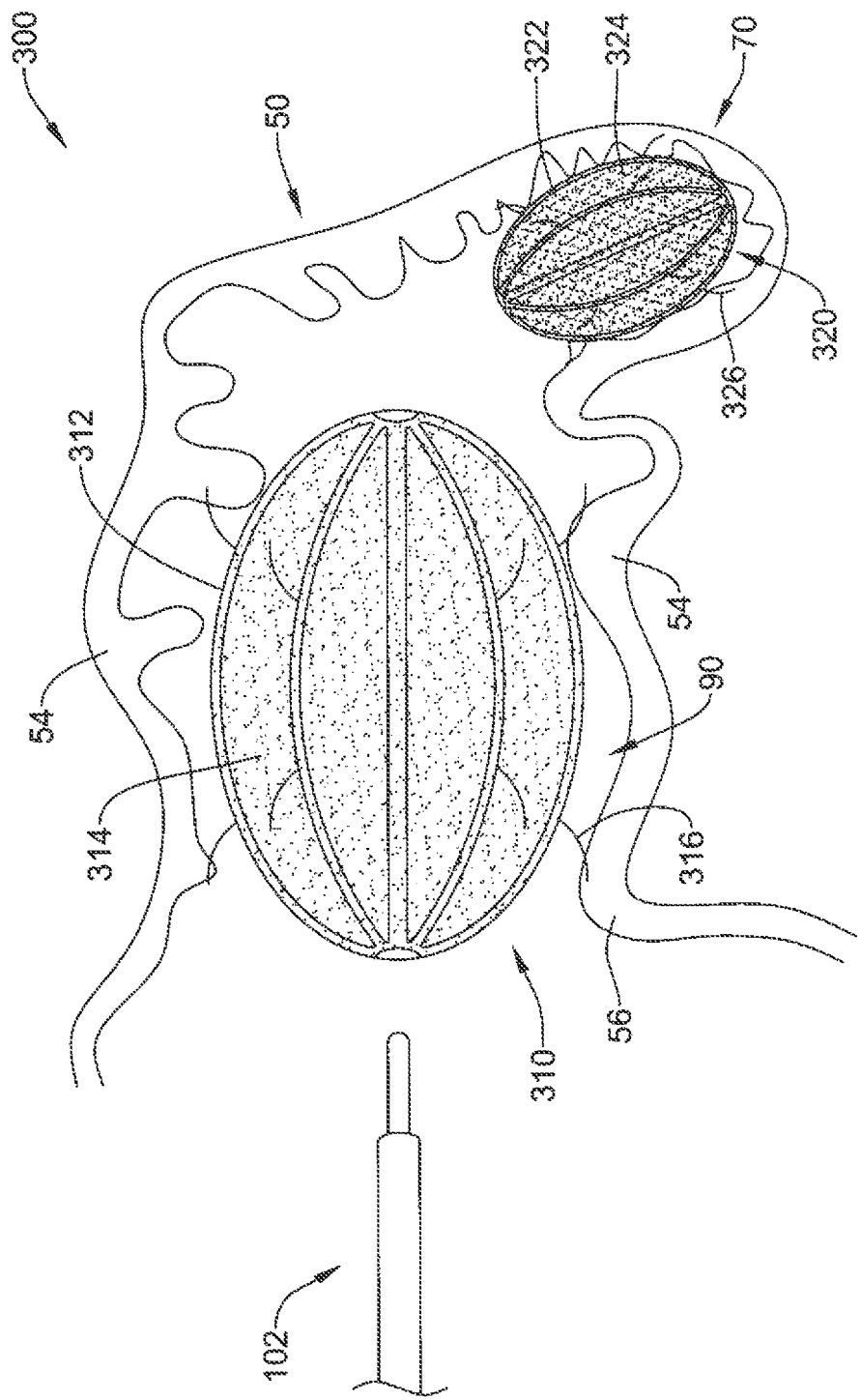
FIG. 8 illustrates a plurality of the example medical device of FIG. 3 disposed within the example left atrial appendage of FIG. 2.

FIG. 8 illustrates an example medical device 300 including an elongate shaft 102 having a distal portion, a first volume-reducing means 310 expandable from a collapsed state to an expanded state, the first volume-reducing means 310 being releasably attached to the distal portion of the elongate shaft 102, and a second volume-reducing means 320 expandable from a collapsed state to an expanded state, the second volume-reducing means 320 being releasably attached to the distal portion of the elongate shaft 102. In some embodiments, the first volume-reducing means 310 may include a first actuatable support frame 312 and a first impermeable covering 314 disposed over the first actuatable support frame 312. In some embodiments, the second volume-reducing means 320 may include a second actuatable support frame 322 and a second impermeable covering 324 disposed over the second actuatable support frame 322.

In some embodiments, the first volume-reducing means 310 may be sized and configured to fit within the left atrial appendage 50 in the expanded state while maintaining an open fluid flow path 90 from a distal region of the left atrial appendage 50 through an ostium 56 of the left atrial appendage 50. In some embodiments, the second volume-reducing means 320 may be sized and configured to be placed within and substantially occlude a distalmost region 70 of the left atrial appendage 50.

In some embodiments the first volume-reducing means 310 may include a first anchoring means configured to engage the lateral wall 54 of the left atrial appendage 50. In some embodiments, the first anchoring means may include a plurality of first anchoring members 316 extending outwardly from an outer surface of the first volume-reducing means 310. In some embodiments, the plurality of first anchoring members 316 may each include a means of limiting penetration of the plurality of first anchoring members 316 into the lateral wall 54 of the left atrial appendage 50. In some embodiments, the plurality of first anchoring members 316 may be configured to rest against a surface of the lateral wall 54. In some embodiments, the plurality of first anchoring members 316 may be configured to penetrate the lateral wall 54. In some embodiments, the plurality of first anchoring members 316 may each include a first portion that is configured to penetrate the lateral wall 54 and a second portion that is configured to rest against a surface of the lateral wall 54. In some embodiments, the plurality of first anchoring members 316 may maintain the first volume-reducing means 310 is a spaced-apart relationship with the lateral wall 54 of the left atrial appendage 50. In many respects, the plurality of first anchoring members 316 may be formed the same and function the same as the plurality of anchoring members 120 described above, with substantially similar or the same features, materials, and construction.

In some embodiments the second volume-reducing means 320 may include a second anchoring means configured to engage a lateral wall 74 of the distalmost region 70 of the left atrial appendage 50. In some embodiments, the second anchoring means may include a plurality of second anchoring members 326 extending outwardly from an outer surface of the second volume-reducing means 320. In some embodiments, the plurality of second anchoring members 326 may each include a means of limiting penetration of the plurality of second anchoring members 326 into the lateral wall 74 of the distalmost region 70. In some embodiments, the plurality of second anchoring members 326 may be configured to rest against a surface of the lateral wall 74. In some embodiments, the plurality of second anchoring members 326 may be configured to penetrate the lateral wall 74. In some embodiments, the plurality of second anchoring members 326 may each include a first portion that is configured to penetrate the lateral wall 74 and a second portion that is configured to rest against a surface of the lateral wall 74. In many respects, the plurality of second anchoring members 326 may be formed the same and function the same as the plurality of anchoring members 120 described above, with substantially similar or the same features, materials, and construction.

In use, the first volume-reducing means 310 and the second volume-reducing means 320 may complement each other's function(s), while further reducing the interior volume of the left atrial appendage 50. The first volume-reducing means 310 may be positioned in a spaced-apart relationship with the lateral wall 54, thereby reducing the volume of the left atrial appendage 50 while maintaining the open fluid flow path 90 from a distal region of the left atrial appendage 50 through the ostium 56 of the left atrial appendage 50. In some embodiments, the open fluid flow path 90 is disposed between an outer surface of the first volume-reducing means 310 and the lateral wall 54 of the left atrial appendage 50. In some embodiments, the first volume-reducing means 310 is configured to maintain the open fluid flow path 90 during an entire cycle of the heart 10. The second volume-reducing means 320 may substantially occlude the distalmost region 70 of the left atrial appendage 50.

Figure 9:
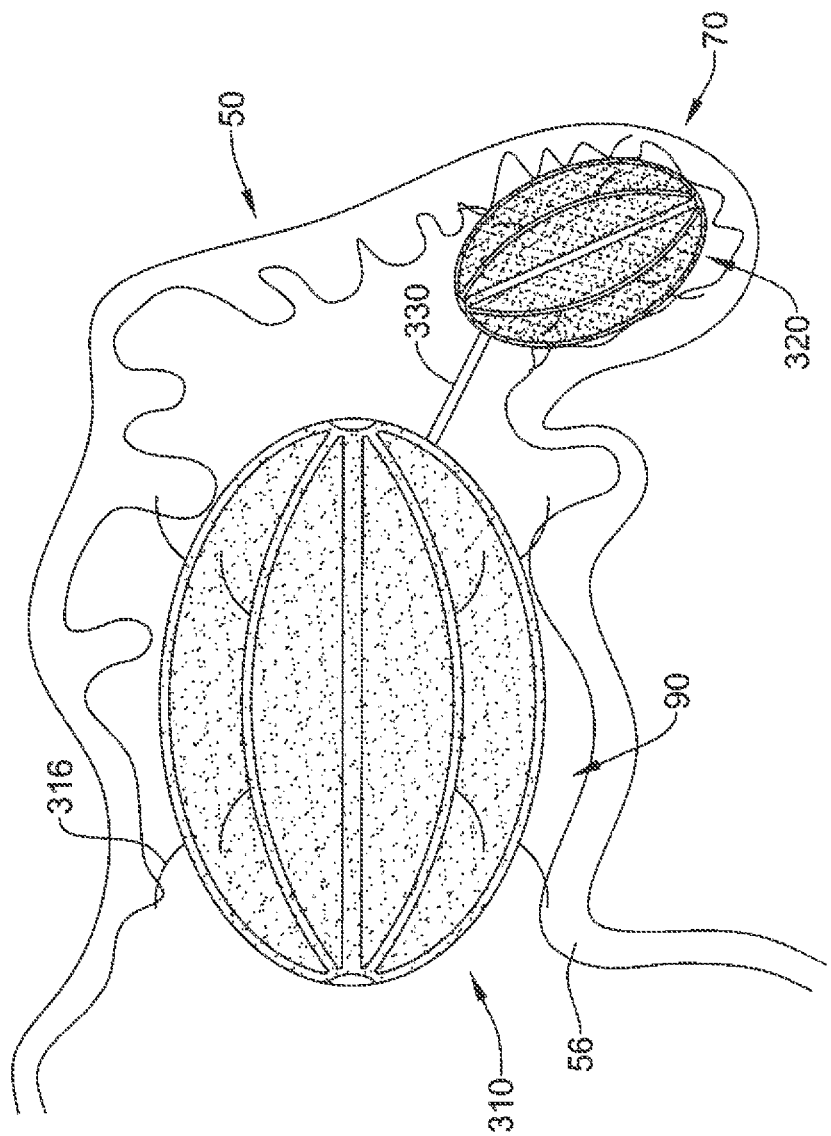
FIG. 9 illustrates a plurality of the example medical device of FIG. 3 disposed within the example left atrial appendage of FIG. 2.
Figure 10A:
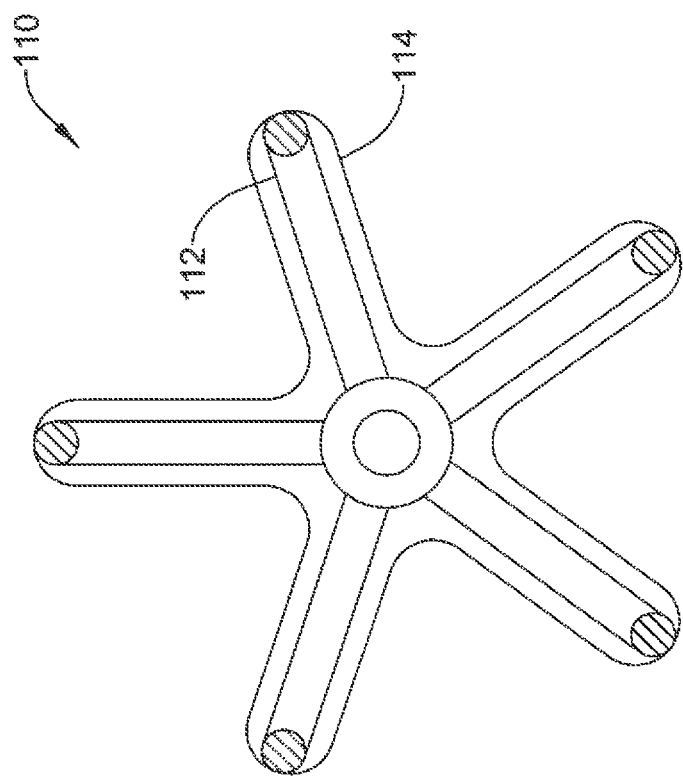
FIGS. 10A-10D are schematic partial cross-sectional views of alternative cross-sectional shapes for the example medical device of FIG. 3.
Figure 10B:
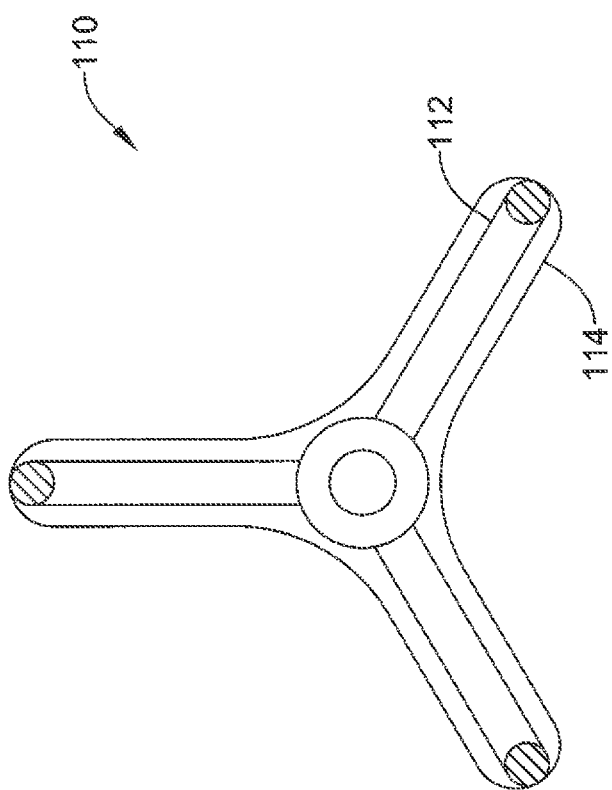
Figure 10C:
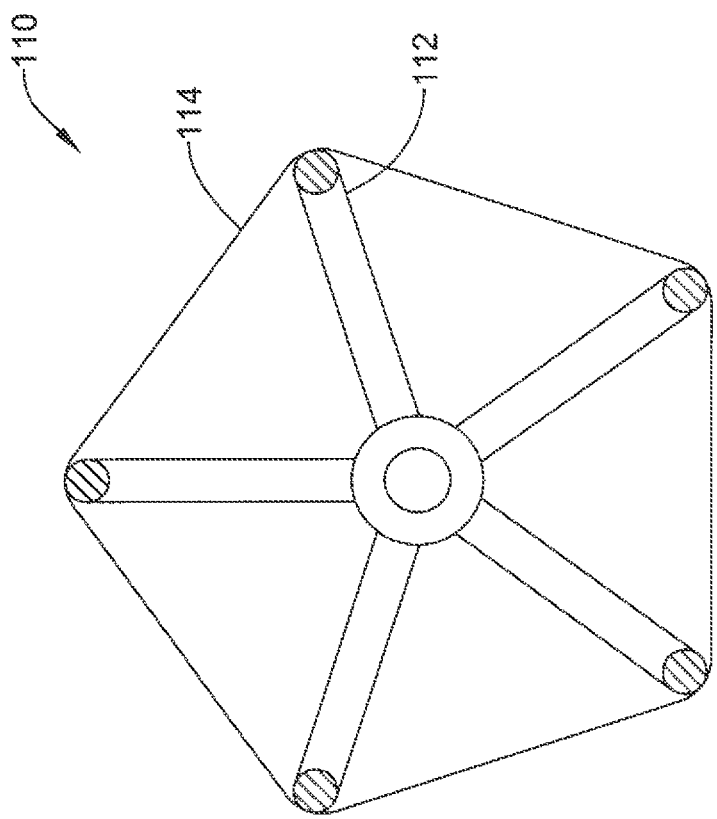
Figure 10D:
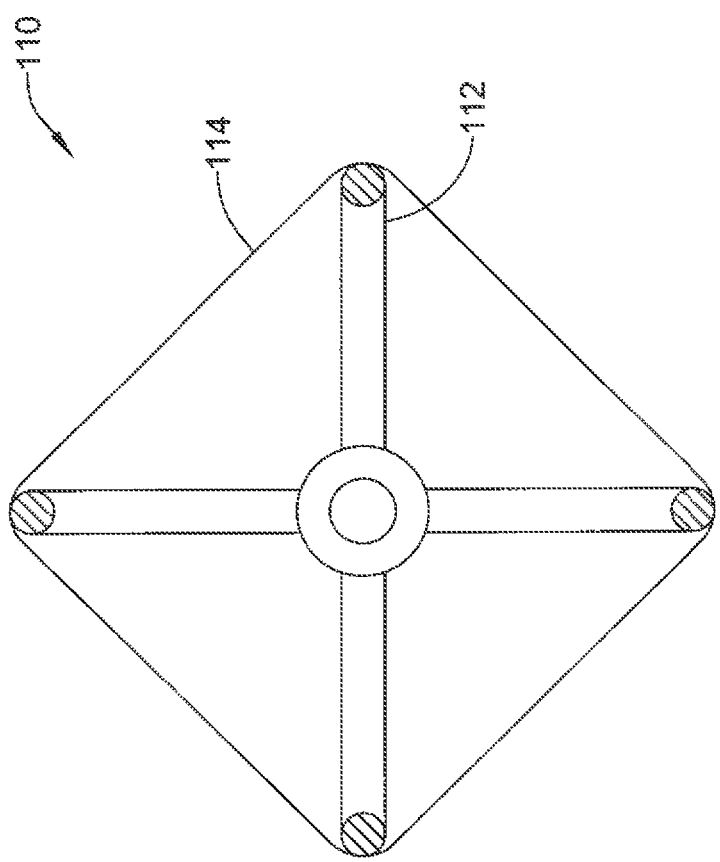

In some embodiments, the first volume-reducing means 310 may be fixedly attached to the second volume-reducing means 320. In some embodiments, the first volume-reducing means 310 may be fixedly attached to the second volume-reducing means 320 by a rigid or semi-rigid connector 330, as shown in FIG. 9. In some embodiments, the connector 330 may serve as the anchoring means of the first volume-reducing means 310, while the plurality of first anchoring members 316 may serve as centering members for the first volume-reducing means 310.

FIGS. 10A-10D illustrate alternate shapes and support strut configurations for the volume-reducing means 110/310/320 disclosed herein. As will be appreciated by the skilled artisan, the volume-reducing means described above, while illustratively shown with 8 support struts forming a volume-reducing means 110/310/320 having a generally spherical or ellipsoid shape, are not so limited. The volume-reducing means are contemplated to have 3, 4, 5, 6, 7, 8, or more individual support struts within the actuatable support frame 112/312/322. Other shapes are contemplated, including but not limited to, prismatic or polygonal shapes such as a pentagonal prism, a hexagonal prism, a triangular prism, a cylinder, a pyramid or tetrahedron, etc. In some embodiments, the support struts may rest directly against the lateral wall 54 of the left atrial appendage 50. In such embodiments, the volume-reducing means may have a scalloped impermeable covering or an impermeable covering which clings tightly to or is adhered to the individual support struts so as to provide a plurality of open fluid flow paths from the distal region of the left atrial appendage 50 through the ostium 56 of the left atrial appendage 50.

As may be seen in FIGS. 11A-11D, in some embodiments, the plurality of anchoring members 120 may each include a means of limiting penetration 122 of the plurality of anchoring members 120 into the lateral wall 54 of the left atrial appendage 50. While FIGS. 11A-11D illustrate certain selected examples of a means of limiting penetration 122, the skilled artisan will understand that other means of limiting penetration 122 will be encompassed by the disclosure and examples provided herein.

Figure 11A:
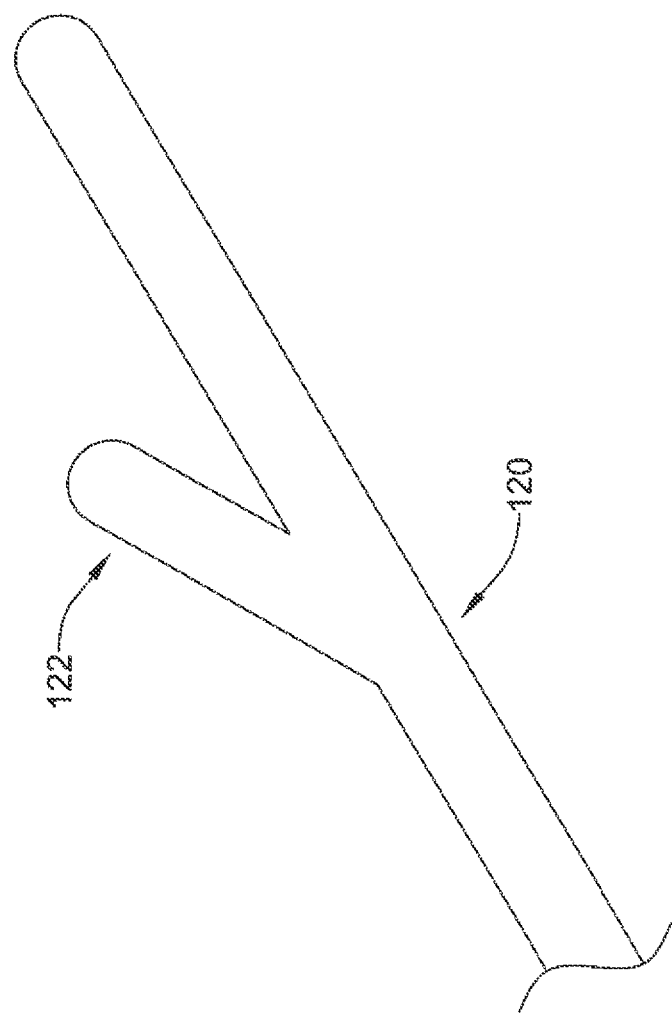

FIG. 11A illustrates an example anchoring member 120 having a means of limiting penetration 122 including a leg or foot protruding at an angle away from the anchoring member 120. In some embodiments, the leg or foot may be shorter in length than the anchoring member 120, and may be configured to rest against a surface of the lateral wall 54, thereby limiting penetration of the anchoring member 120 into the lateral wall 54.

FIG. 11B illustrates an example anchoring member 120 having a means of limiting penetration 122 including a plurality of legs or feet protruding at an angle away from the anchoring member 120. In some embodiments, the plurality of legs or feet may each be shorter in length than the anchoring member 120, and may be configured to rest against a surface of the lateral wall 54, thereby limiting penetration of the anchoring member 120 into the lateral wall 54. As will be appreciated by the skilled artisan, while the illustrative example shows two legs or feet, a higher quantity may be used without departing from the scope of the disclosure. An anchoring member 120 having 2, 3, 4, 5, 6, or more legs or feet is contemplated, depending upon the intended use.

Figure 11C:
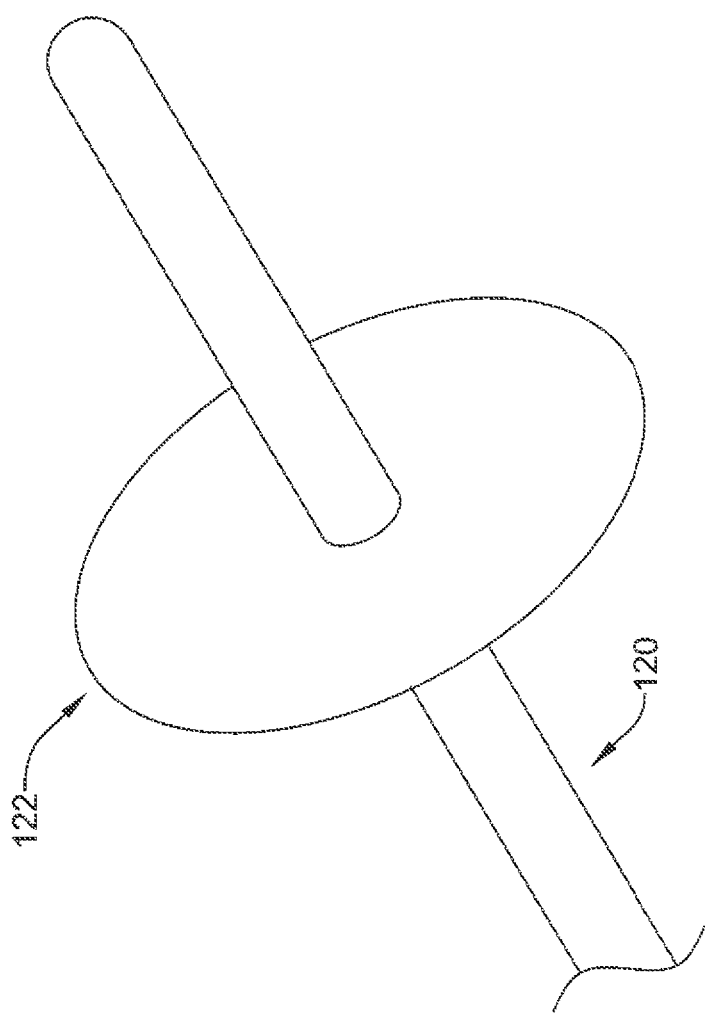
Figure 11D:
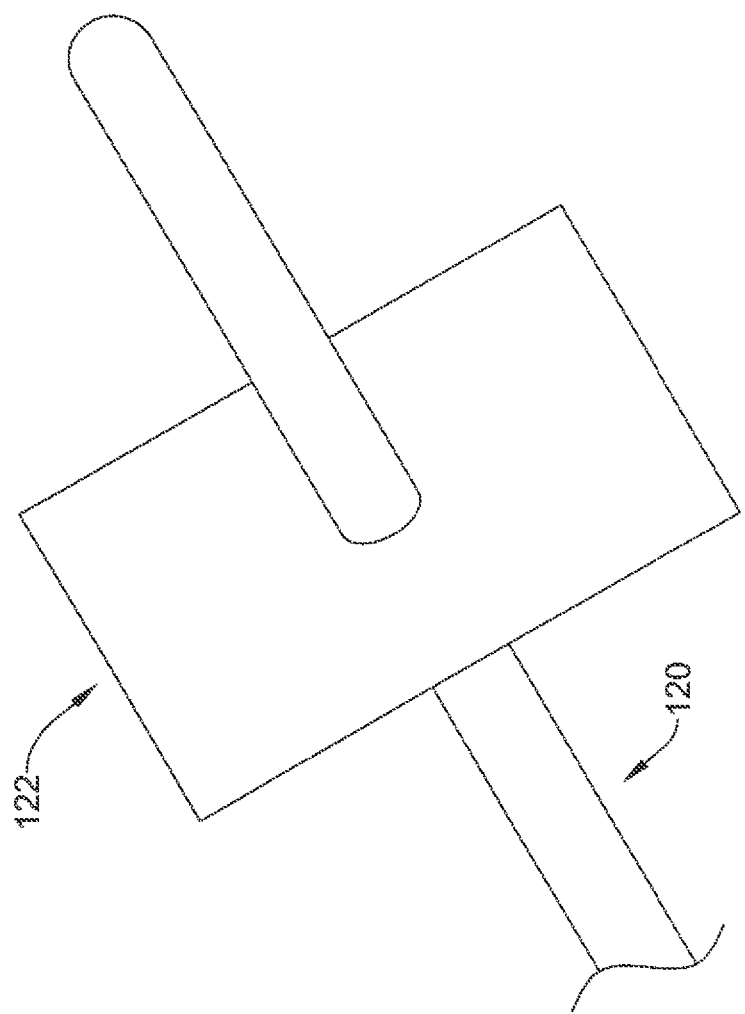

FIGS. 11C and 11D illustrate an example anchoring member 120 having a means of limiting penetration 122 including a flattened landing pad disposed about and fixed to the anchoring member 120. The flattened landing pad is configured to rest against a surface of the lateral wall 54, thereby limiting penetration of the anchoring member 120 into the lateral wall 54. In some embodiments, an outer diameter of the flattened landing pad may be 2, 3, 4, 5, 10, or more times greater than an outer diameter of the anchoring member 120. Illustratively, FIG. 11C shows a generally circular landing pad and FIG. 11D shows a generally square landing pad. However, the means of limiting penetration 122 is not limited to these two shapes, and the skilled artisan will understand that other or additional polygonal or irregular shapes may be used, including but not limited to, triangular, rectangular, elliptical, pentagonal, hexagonal, octagonal, etc.

As discussed above, the plurality of first anchoring members 316 and the plurality of second anchoring members 326 may include substantially similar or the same features, materials, and construction as the plurality of anchoring members 120.

In some embodiments, the plurality of struts of the actuatable support frame 112/312/322 and/or the plurality of anchoring members 120/316/326 may be formed of or include a metallic material, a metallic alloy, a ceramic material, a rigid or high performance polymer, a metallic-polymer composite, combinations thereof, and the like. Some examples of some suitable materials may include metallic materials and/or alloys such as stainless steel (e.g. 304v stainless steel or 316L stainless steel), nickel-titanium alloy (e.g., nitinol, such as super elastic or linear elastic nitinol), nickel-chromium alloy, nickel-chromium-iron alloy, cobalt alloy, nickel, titanium, platinum, or alternatively, a polymer material, such as a high performance polymer, or other suitable materials, and the like. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

In some embodiments, the plurality of struts of the actuatable support frame 112/312/322 and/or the plurality of anchoring members 120/316/326 may be mixed with, may be doped with, may be coated with, or may otherwise include a radiopaque material. Radiopaque materials are understood to be materials capable of producing a relatively bright image on a fluoroscopy screen or another imaging technique such as X-ray during a medical procedure. This relatively bright image aids the user of device in determining its location. Suitable radiopaque materials may include, but are not limited to, bismuth subcarbonate, iodine, gold, platinum, palladium, tantalum, tungsten or tungsten alloy, and the like.

In some embodiments, the impermeable covering 114/314/324 may be formed of or include a polymeric material, a metallic or metallic alloy material, a metallic-polymer composite, combinations thereof, and the like. Examples of suitable polymers may include polyurethane, a polyether-ester such as ARNITEL® available from DSM Engineering Plastics, a polyester such as HYTREL® available from DuPont, a linear low density polyethylene such as REXELL®, a polyamide such as DURETHAN® available from Bayer or CRISTAMID® available from Elf Atochem, an elastomeric polyamide, a block polyamide/ether, a polyether block amide such as PEBA available under the trade name PEBAX®, silicones, polyethylene, Marlex high-density polyethylene, polyetheretherketone (PEEK), polyimide (PI), and polyetherimide (PEI), a liquid crystal polymer (LCP) alone or blended with other materials.

In some embodiments, the medical device 100/300 and/or the volume-reducing means 110/310/320 may be made from, may be mixed with, may be coated with, or may otherwise include a material that provides a smooth, slick outer surface. In some embodiments, the medical device 100/300 and/or the volume-reducing means 110/310/320 may include or be coated with a lubricious coating, a hydrophilic coating, a hydrophobic coating, a drug-eluting material, an anti-thrombus coating, or other suitable coating depending on the intended use or application.

A method of reducing the volume of a left atrial appendage 50 of a heart 10, the left atrial appendage 50 having a generally longitudinal axis 52, a lateral wall 54, and an ostium 56 forming a proximal mouth 58 thereof, may comprise obtaining a medical device 100 including an elongate shaft 102 having a distal portion 104, and a volume-reducing means 110 expandable from a collapsed state to an expanded state, the volume-reducing means 110 being releasably attached to the distal portion 104, wherein the volume-reducing means 110 includes an actuatable support frame 112 and an impermeable covering 114 disposed over the actuatable support frame 112, wherein the volume-reducing means 110 is sized to fit within the left atrial appendage 50 in the expanded state. The method may further include advancing the medical device 100 percutaneously toward the heart 10, inserting the volume-reducing means 110 through the ostium 56 and into the left atrial appendage 50 in the collapsed state, actuating the actuatable support frame 112 to expand the volume-reducing means 110 to the expanded state, introducing an inflation medium into an interior of the volume-reducing means 110, positioning the volume-reducing means 110 such that an open fluid flow path 90 from a distal region of the left atrial appendage 50 through the ostium 56 of the left atrial appendage 50 is maintained through an entire cycle of the heart 10, detaching the volume-reducing means 110 from the distal portion 104 of the elongate shaft 102, and withdrawing the elongate shaft 102 from the heart 10.

The method may include an open fluid flow path 90 disposed between an outer surface of the volume-reducing means 110 and the lateral wall 54 of the left atrial appendage 50. In some embodiments, the method may include the volume-reducing means 110 being sized to reduce the volume of the left atrial appendage 50 by at least 40%, 50%, 65%, 75%, 90%, or other suitable amounts. In some embodiments, the volume-reducing means 110 of the method further includes an anchoring means configured to engage the lateral wall 54 of the left atrial appendage 50. In some embodiments, the step of positioning the volume-reducing means 110 includes engaging the anchoring means with the lateral wall 54 of the left atrial appendage 50. In some embodiments, the anchoring means of the method may include a plurality of anchoring members 120 extending outwardly from an outer surface of the volume-reducing means 110. In some embodiments, the plurality of anchoring members 120 each include a means of limiting penetration 122 of the plurality of anchoring members 120 into the lateral wall 54 of the left atrial appendage 50. In some embodiments, the plurality of anchoring members 120 maintains the volume-reducing means 110 in a spaced-apart relationship with the lateral wall 54 of the left atrial appendage 50.

It should be understood that although the above discussion was focused on a medical device and methods of use within the vascular system of a patient, other embodiments of medical devices or methods in accordance with the disclosure can be adapted and configured for use in other parts of the anatomy of a patient. For example, devices and methods in accordance with the disclosure can be adapted for use in the digestive or gastrointestinal tract, such as in the mouth, throat, small and large intestine, colon, rectum, and the like. For another example, devices and methods can be adapted and configured for use within the respiratory tract, such as in the mouth, nose, throat, bronchial passages, nasal passages, lungs, and the like. Similarly, the apparatus and/or medical devices described herein with respect to percutaneous deployment may be used in other types of surgical procedures as appropriate. For example, in some embodiments, the medical devices may be deployed in a non-percutaneous procedure, such as an open heart procedure. Devices and methods in accordance with the invention can also be adapted and configured for other uses within the anatomy.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

We claim:

1. A volume reducing device for a left atrial appendage comprising:
    a distal hub;
    a proximal hub,
    the distal hub and the proximal hub defining a longitudinal axis therebetween;
    an actuatable support frame which includes a plurality of struts extending from the distal hub to the proximal hub,
    wherein the actuatable support frame has a radially collapsed configuration and a radially expanded configuration defining an interior volume sized and configured to fit within the left atrial appendage;
    an impermeable covering supported by the actuatable support frame,
    wherein the impermeable covering prevents blood from entering the interior volume of the radially expanded configuration of the actuatable support frame; and
    a plurality of anchoring members which extend radially outward from the plurality of struts of the actuatable support frame,
    wherein the plurality of anchoring members is configured and adapted to anchor and position the volume reducing device in a spaced-apart relationship with a lateral wall of the left atrial appendage when the actuatable support frame is actuated to assume the radially expanded configuration within the left atrial appendage thereby reducing a volume of the left atrial appendage while maintaining an open fluid flow path from a distal region of the left atrial appendage through the ostium of the left atrial appendage and between the impermeable covering and the lateral wall of the left atrial appendage.

2. The volume reducing device of claim 1, wherein the actuatable support frame is mechanically actuated.

3. The volume reducing device of claim 2, wherein the actuatable support frame is mechanically actuated by filling the interior volume of the actuatable support frame with a fluid.

4. The volume reducing device of claim 3, wherein the fluid is adapted to solidify within the interior volume of the actuatable support frame.

5. The volume reducing device of claim 1, wherein the actuatable support frame is self-expanding.

6. The volume reducing device of claim 1, wherein the volume reducing device is sized to reduce the volume of the left atrial appendage in which it is deployed by at least 40%.

7. The volume reducing device of claim 1, wherein the volume reducing device is sized to reduce the volume of the left atrial appendage in which it is deployed by at least 65%.

8. The volume reducing device of claim 1, wherein the volume reducing device is sized to reduce the volume of the left atrial appendage in which it is deployed by at least 90%.

9. The volume reducing device of claim 1, further comprising an elongate shaft having a distal portion releasably coupled to the proximal hub.

10. The volume reducing device of claim 9, wherein the elongate shaft includes an inflation lumen in fluid communication with the interior volume of the actuatable support frame.

11. The volume reducing device of claim 1, wherein the volume reducing device is sized and adapted to fit within the left atrial appendage and adjacent to an ostium of the left atrial appendage in the radially expanded configuration.

12. The volume reducing device of claim 11, further comprising a second volume reducing device sized and adapted to fit within a distalmost region of the left atrial appendage,
    wherein the second volume reducing device comprises a second distal hub, a second proximal hub, a second actuatable support frame, a second impermeable covering which prevents blood from entering the interior volume of an expanded configuration of the second actuatable support frame, and a second plurality of anchoring members which extend radially outward from the second actuatable support frame, the second plurality of anchoring members being configured and adapted to anchor and position the second volume reducing device in a spaced-apart relationship with a lateral wall of the distalmost region of the left atrial appendage when the second actuatable support frame is actuated.

13. The volume reducing device of claim 12, wherein the volume reducing device is connected to the second volume reducing device by a connector.

14. The volume reducing device of claim 12, wherein the second plurality of anchoring members maintain an open fluid flow path between the second impermeable covering and the lateral wall of the left atrial appendage.

15. A method of reducing a volume of a left atrial appendage while maintaining fluid communication between the left atrial appendage and a left atrium comprising:
    advancing a volume reducing device sized and adapted to fit within the left atrial appendage, wherein the volume reducing device comprises an a distal hub, a proximal hub, an elongate shaft releasably coupled to the proximal hub, an actuatable support frame connected to the distal hub and the proximal hub, a impermeable covering supported by the actuatable support frame, which prevents blood from entering an interior volume of an expanded configuration of the actuatable support frame, and a plurality of anchoring members which extend radially outward from the actuatable support frame, the plurality of anchoring members being configured and adapted to anchor and position the volume reducing device in a spaced-apart relationship with a lateral wall of the left atrial appendage when the actuatable support frame is actuated;

positioning the volume reducing device within the left atrial appendage of a patient;

actuating the actuatable support frame from a radially collapsed configuration to a radially expanded configuration within the left atrial appendage, thereby reducing the volume of the left atrial appendage; engaging the lateral wall of the left atrial appendage with the plurality of anchoring members in a spaced-apart relationship with the impermeable covering thereby maintaining an open fluid flow path from a distal region of the left atrial appendage through the ostium of the left atrial appendage and between the impermeable covering and the lateral wall of the left atrial appendage;

releasing the elongate shaft releasably coupled to the proximal hub from the proximal hub; and removing the released elongated shaft from the patient.

16. The method of claim 15, wherein the volume of the left atrial appendage is reduced by at least 40%.

17. The method of claim 15, wherein the volume of the left atrial appendage is reduced by at least 65%.

18. The method of claim 15, wherein the volume of the left atrial appendage is reduced by at least 90%.

19. The method of claim 15, wherein the volume reducing device includes a second volume reducing device located distal of the volume reducing device, the second volume reducing device being sized and adapted to fit within a distalmost region of the left atrial appendage in a radially expanded configuration within the left atrial appendage while maintaining an open fluid flow path between the second volume reducing device and the lateral wall of the left atrial appendage.

20. The method of claim 19, wherein the volume reducing device is connected to the second volume reducing device.

* * * * *